United States Patent [19]

Coates et al.

[11] Patent Number: 5,118,686
[45] Date of Patent: Jun. 2, 1992

[54] PHENYLPYRIMIDONES

[75] Inventors: William J. Coates, Welwyn Garden City; Derek A. Rawlings, Stevenage, both of England

[73] Assignee: Smith Kline & French Laboratories Limited, Welwyn Garden City, England

[21] Appl. No.: 514,788

[22] Filed: Apr. 25, 1990

[30] Foreign Application Priority Data

Apr. 26, 1989 [GB] United Kingdom ............... 8909560

[51] Int. Cl.$^5$ .................. A61K 31/505; C07D 239/22
[52] U.S. Cl. ..................................... 514/269; 544/319
[58] Field of Search ........................ 544/319; 514/269

[56] References Cited

U.S. PATENT DOCUMENTS

| | | | |
|---|---|---|---|
| 3,660,403 | 5/1972 | Shen et al. | 260/251 |
| 3,745,161 | 7/1973 | Shen et al. | 260/250 |
| 3,883,653 | 5/1975 | Barth | 424/251 |
| 4,031,093 | 6/1977 | Juby et al. | 260/251 R |
| 4,082,751 | 4/1978 | Juby et al. | 260/256.4 |
| 4,209,623 | 6/1980 | Juby | 544/319 |
| 4,241,056 | 12/1980 | Wetzel et al. | 424/226 |

OTHER PUBLICATIONS

Juby et al., J. Med. Chem., 1982, 25, 1145–1150.
Juby et al., J. Med. Chem., 1979, 22, 263.
Omori et al, "2-substituted 4-methyl, etc" CA 80: 108569h (1974).
Miyazaki et al, "2-substituted-4-methyl, etc." CA 79: 146554m (1973).
Kheifets et al, "Reaction of 4,6-dioxopyrimidines, etc" CA 85: 77435h (1976).
Teraji et al, "Dihydropyrimidine derivatives, etc" CA 98: 89382v (1983).

Primary Examiner—Patricia L. Morris
Attorney, Agent, or Firm—Linda E. Hall; Stuart R. Suter; Edward T. Lentz

[57] ABSTRACT

This invention relates to phenylpyrimidone derivatives which have bronchodilator activity. A compound of the invention is 4-cyano-6-hydroxy-2-(2-propoxyphenyl)pyrimidine.

12 Claims, No Drawings

PHENYLPYRIMIDONES

The present invention relates to phenylpyrimidone derivatives, pharmaceutical compositions containing them and methods of therapy by administering them. The compounds of this invention are inhibitors of a calmodulin insensitive cyclic GMP phosphodiesterase and are of use in combatting such conditions where such inhibition is thought to be beneficial. They are bronchodilators and are therefore of use in combatting chronic reversible obstructive lung diseases such as asthma and bronchitis. Furthermore they are vasodilators and are therefore of value in combatting angina, hypertension and congestive heart failure. They are of use in the treatment of gastrointestinal motility disorders, for example irritable bowel syndrome.

U.S. Pat. Nos. 3660403 and 3745161 disclose compounds of the general formula (A):

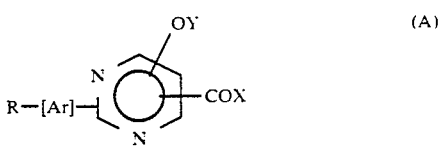

wherein COX and OY are ortho to each other and [Ar] is para to either COX or OY, R is inter alia lower alkoxy, [Ar] is inter alia phenyl, X is inter alia hydroxy, amino, alkylamino, dialkylamino or alkoxy, and Y is inter alia hydrogen. These compounds are described as having anti-inflammatory, anti-pyretic and analgesic activity. None of the compounds of the present invention are specifically disclosed.

U.S. Pat. No. 4031093 discloses anti-allergic compounds of the formula (B):

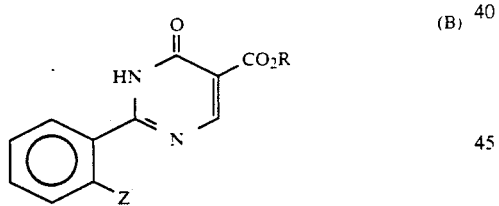

wherein Z is inter alia $C_{2-6}$alkoxy or $C_{2-6}$alkenyloxy and R is hydrogen or the residue of an easily cleavable ester group.

U.S. Pat. No. 4082751 discloses anti-allergic compounds of the formula (C):

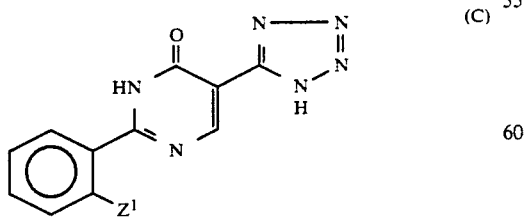

wherein $Z^1$ is inter alia lower alkoxy or lower alkenyloxy.

U.S. Pat. No. 4082751 also discloses intermediate compounds of the formula (D):

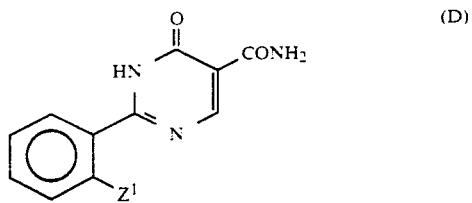

wherein $Z^1$ is as hereinbefore defined. In J. Med. Chem. 1982, 1145–1150 it is indicated at page 1148 that the compounds of the formula (D) have insignificant antiallergic activity.

U.S. Pat. No. 4241056 discloses 3-(4-hydroxy-5-pyrimidyl)-ureido-penicillins. As intermediates for such compounds are described compounds of the general formula (E):

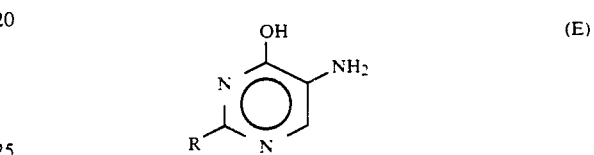

wherein R is inter alia phenyl optionally substituted by $C_{1-4}$alkoxy. None of the compounds of the present invention are specifically disclosed.

According to the present invention there is provided compounds of the formula (1):

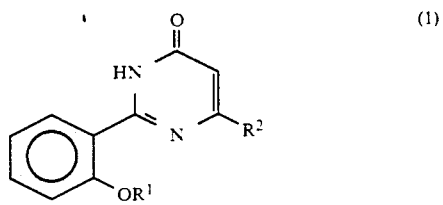

and pharmaceutically acceptable salts thereof, wherein
 $R^1$ is $C_{1-6}$alkyl, $C_{2-6}$alkenyl, $C_{3-5}$cycloalkyl$C_{1-6}$alkyl, phenyl$C1-6$alkyl or $C1-6$alkyl substituted by 1 to 6 fluoro groups; and
 $R^2$ is $C1-6$alkyl, phenyl, hydroxy, $C1-6$alkoxy, halo, —NHCOR$^3$, —NHCONHR$^4$, 5-tetrazolyl, —CO$_2$R$^5$, cyano, —CONR$^6$R$^7$, or —NR$^8$R$^9$ Wherein $R^3$ to $R^7$ are independently hydrogen or C1-6alkyl and $R^8$ and $R^9$ are independently hydrogen or C1-6alkyl optionally substituted by hydroxy provided that the carbon atom adjacent to the nitrogen atom is not substituted by hydroxy.

Suitably $R^1$ is $C_{2-5}$alkyl for example isopropyl, butyl, isobutyl or pentyl.

Suitably $R^1$ is $C_{3-5}$alkenyl for example allyl, butenyl or pentenyl.

Suitably $R^1$ is cyclopropylmethyl or benzyl.

Examples of C1-6alkyl substituted by 1 to 6 fluoro groups include —CF$_3$, —CH$_2$CF$_3$ or —CF$_2$CHFCF$_3$.

Preferably $R^1$ is n-propyl.

Suitably $R^2$ is phenyl or $C_{1-6}$alkyl for example methyl, ethyl, propyl or butyl.

Suitably $R^2$ is hydroxy, C1-6alkoxy for example methoxy, ethoxy or propoxy, or halo for example fluoro, chloro, bromo or iodo.

Suitably $R^2$ is —NHCOR$^3$ for example formamido, acetamido, propionamido or butyramido.

Suitably $R^2$ is —NHCONHR$^4$ for example ureido or N-methylureido.

Suitably $R^2$ is 5-tetrazolyl or —CO$_2$R$^5$ for example carboxy, methoxycarbonyl or ethoxycarbonyl.

Suitably $R^2$ is —cyano or —CONR$^6$R$^7$ for example carboxamido, N-methylcarboxamido, N-ethylcarboxamido or N-propylcarboxamido.

Suitably $R^2$ is —NR$^8$R$^9$ for example amino, methylamino, ethylamino, propylamino, 2-hydroxyethylamino, 3-hydroxypropylamino or bis-(2-hydroxyethyl)amino.

Specific compounds of this invention are :
6-amino-2-(2-propoxyphenyl)pyrimidin-4[3H]-one,
6-acetamido-2-(2-propoxyphenyl)pyrimidin-4[3H]-one,
6-propionamido-2-(2-propoxyphenyl)pyrimidin-4[3H]-one,
6-butyramido-2-(2-propoxyphenyl)pyrimidin-4[3H]-one,
6-N'-methylureido-2-(2-propoxyphenyl)pyrimidin-4[3H]-one,
4,6-dihydroxy-2-(2-propoxyphenyl)pyrimidine,
4-chloro-6-hydroxy-2-(2-propoxyphenyl)pyrimidine,
6-ethylamino-2-(2-propoxyphenyl)pyrimidin-4[3H]-one,
6-propylamino-2-(2-propoxyphenyl)pyrimidin-4[3H]-one,
6-(2-hydroxyethylamino)-2-(2-propoxyphenyl)-pyrimidin[4[3H]-one,
6-(3-hydroxypropylamino)-2-(2-propoxyphenyl)pyrimidin 4[3H]-one,
4-hydroxy-6-methyl-2-(2-propoxyphenyl)pyrimidine,
6-hydroxy-2-(2-propoxyphenyl)pyrimidine-4-carboxylic acid,
ethyl 6-hydroxy-2-(2-propoxyphenyl)pyrimidine-4-carboxylate,
6-hydroxy-2-(2-propoxyphenyl)pyrimidine-4-carboxamide,
4-cyano-6-hydroxy-2-(2-propoxyphenyl)pyrimidine,
2-(2-propoxyphenyl)-6-(IH-tetrazol-5-yl)pyrimidin-4(3H)-one,
4-ethyl-6-hydroxy-2-(2-propoxyphenyl)pyrimidine,
4-hydroxy-6-phenyl-2-(2-propoxyphenyl)pyrimidine,
N-methyl 6-hydroxy-2-(2-propoxyphenyl)pyrimidine-4-carboxamide,
N-ethyl 6-hydroxy-2-(2-propoxyphenyl)pyrimidine-4-carboxamide,
N-propyl 6-hydroxy-2-(2-propoxyphenyl)pyrimidine-4-carboxamide,
6-ethoxy-2-(2-propoxyphenyl)pyrimidin-4(3H)-one, or
6-N,N-bis-(2-hydroxyethyl)amino-2-(2-propoxyphenyl)pyrimidin-4(3H)-one,
or pharmaceutically acceptable salts thereof.

This invention covers all tautomeric and optical isomeric forms of compounds of formula (1).

Compounds of the formula (1) wherein $R^2$ is —NR$^8$R$^9$ may form pharmaceutically acceptable salts with acids such as hydrochloric, hydrobromic, sulphuric and phosphoric acids.

Compounds of the formula (1) may form pharmaceutically acceptable salts with metal ions, such as alkali metals for example sodium and potassium, or with an ammonium ion.

In order to use a compound of the formula (1) or a pharmaceutically acceptable salt thereof for the treatment of humans and other mammals it is normally formulated in accordance with standard pharmaceutical practice as a pharmaceutical composition.

Compounds of formula (1) and their pharmaceutically acceptable salts may be administered in standard manner for the treatment of the indicated diseases, for example orally, sub-lingually, parenterally, transdermally, rectally, via inhalation or via buccal administration.

Compounds of formula (!) and their pharmaceutically acceptable salts which are active when given orally or via buccal administration can be formulated as liquids, syrups, tablets, capsules and lozenges. An oral liquid formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, celluloses, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil or solubilising agent, for example polyethylene glycol, polyvinylpyrrolidone, 2-pyrrolidone, cyclodextrin, lecithin, arachis oil, or sesame oil.

A typical suppository formulation comprises a compound of formula (1) or a pharmaceutically acceptable salt thereof which is active when administered in this way, with a binding and/or lubricating agent, for example polymeric glycols, gelatins, cocoa-butter or other low melting vegetable waxes or fats.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane, or are in the form of a powder for insufflation.

Preferably the composition is in unit dosage form, for example a tablet, capsule or metered aerosol dose, so that the patient may administer to himself a single dose.

Each dosage unit for oral administration contains suitably from 0.001 mg/Kg to 30 mg/Kg, and preferably from 0.005 mg/Kg to 15 mg/Kg, and each dosage unit for parenteral administration contains suitably from 0.001 mg/Kg to 10 mg/Kg, of a compound of formula (1) or a pharmaceutically acceptable salt thereof calculated as the free base.

The daily dosage regimen for oral administration is suitably about 0.001 mg/Kg to 120 mg/Kg, of a compound of formula (1) or a pharmaceutically acceptable salt thereof calculated as the free base. The daily dosage regimen for parenteral administration is suitably about 0.001 mg/Kg to 40 mg/Kg, for example about 0.005 mg/Kg to 10 mg/Kg, of a compound of the formula (1)

or a pharmaceutically acceptable salt thereof calculated as the free base. The active ingredient may be administered as required for example from 1 to 8 times a day or by infusion. The compositions of the invention are bronchodilators and are useful in chronic reversible obstructive lung disease for example asthma and bronchitis. The compositions of the present invention are of use in the treatment of gastrointestinal motility disorders, such as irritable bowel syndrome. The compositions of the present invention have vasodilator activity and are of use in the treatment of angina, hypertension and congestive heart failure. Such conditions can be treated by administration orally, sub-lingually, topically, rectally, parenterally or by inhalation. For administration by inhalation dosages are controlled by a valve, are administered as required and for an adult are conveniently in the range 0.1–5.0 mg of a compound of the formula (1) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of the formula (1) are bronchodilators such as sympathomimetic amines for example isoprenaline, isoetharine, sulbutamol, phenylephrine and ephedrine or xanthine derivatives for example theophylline and aminophylline, anti-allergic agents for example disodium cromoglycate, histamine $H_1$-antagonists, vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compounds of the formula (1) or pharmaceutically acceptable salts thereof can be prepared by a process which comprises :

a) for compounds wherein $R^2$ is amino, reacting a compound of the formula (2) :

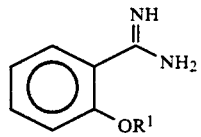

(2)

wherein $R^1$ is as hereinbefore defined with a $C_{1-6}$alkyl cyanoacetate;

b) for compounds wherein $R^2$ is hydroxy, phenyl, $C_{1-6}$alkyl or carboxy, reacting a compound of the formula (2) as hereinbefore defined with a compound of the formula (3) :

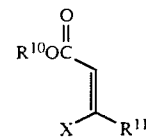

(3)

wherein X is a displaceable group, $R^{11}$ is hydroxy, phenyl, $C_{1-6}$alkyl or carboxy and $R^{10}$ is an ester forming group;

c) for compounds wherein $R^2$ is —NHCOR$^3$, reacting a compound of the formula (1) wherein $R^2$ is amino with a formulating agent or a $C_{2-7}$alkanoylating agent;

d) for compounds wherein $R^2$ is —NHCONHR$^4$ in which $R^4$ is $C_{1-6}$alkyl, reacting a compound of the formula (1) wherein $R^2$ is amino with a $C_{1-6}$alkyl isocyanate;

e) for compounds wherein $R^2$ is —NHCONH$_2$, reacting a compound of the formula (4)

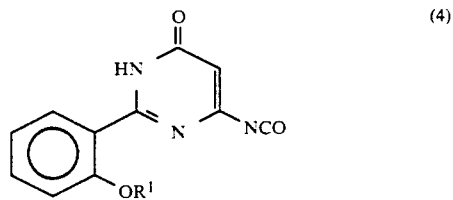

(4)

wherein $R^1$ is as hereinbefore defined with ammonia;

f) for compounds wherein $R^2$ is halo, hydrolysing a compound of the formula (5) :

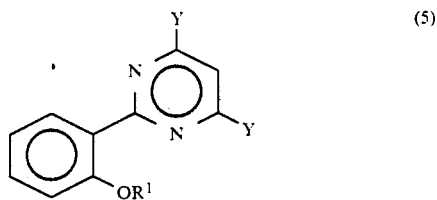

(5)

wherein $R^1$ is as hereinbefore defined and Y is halo;

g) for compounds wherein $R^2$ is —NR$^8$R$^9$, reacting a compound of the formula (1) wherein $R^2$ is halo with an amine HNR$^8$R$^9$ wherein $R^8$ and $R^9$ are as hereinbefore defined;

h) for compounds wherein $R^2$ is —CO$_2$R$^5$ in which $R^5$ is $C_{1-6}$alkyl, reacting a compound of the formula (1) wherein $R^2$ is carboxy with $R^5$OH in which $R^5$ is $C_{1-6}$alkyl in the presence of an acid catalyst;

i) for compounds wherein $R^2$ is —CONR$^6$R$^7$, reacting a compound of the formula (1) wherein $R^2$ is —CO$_2$R$^5$ in which $R^5$ is $C_{1-6}$alkyl with an amine HNR$^6$R$^7$ wherein $R^6$ and $R^7$ are as hereinbefore defined;

j) for compounds wherein $R^2$ is cyano, dehydrating a compound of the formula (1) wherein $R^2$ is —CONH$_2$;

k) for compounds wherein $R^2$ is 5-tetrazolyl, reacting a compound of the formula (1) wherein $R^2$ is cyano with an azide salt; or l) for compounds wherein $R^2$ is $C_{1-6}$alkoxy, reacting a compound of the formula (1) wherein $R^2$ is halo with a $C_{1-6}$alkoxide salt;

and thereafter optionally forming a pharmaceutically acceptable salt.

Suitably a compound of the formula (2) is treated with a $C_{1-6}$alkyl cyanoacetate such as ethyl cyanoacetate or a compound of the formula (3) in water or an organic solvent such as a $C_{1-4}$alkanol or dimethylformamide or mixtures thereof in the presence of a base such as sodium hydroxide, a sodium alkoxide or sodium hydride at ambient or elevated temperature, for example 40°–150° C., conveniently at the reflux temperature of the reaction mixture.

Suitably X is hydroxy or a derivative thereof, for example X is protected hydroxy such as silyloxy, an acid residue (for example $C_{1-6}$alkanoyloxy) or an ether residue (for example methoxy or ethoxy). Suitably $R^{10}$ is $C_{1-6}$alkyl, for example methyl or ethyl. Preferably when $R^{11}$ is hydroxy, $R^{10}$ is ethyl and X is ethoxy, that is a compound of the formula (2) is reacted with diethylmalonate. Preferably when $R^{11}$ is methyl, ethyl or phenyl, $R^{10}$ is ethyl and X is hydroxy, that is a compound of the formula (2) is reacted with ethyl acetoacetate, ethyl propionylacetate or ethyl benzoylacetate. Preferably when $R^{11}$ is carboxy, $R^{10}$ is ethyl and X is hydroxy, that is a compound of the formula (2) is reacted with ethyl 4-oxalacetate.

The reaction between a compound of the formula (1) wherein $R^2$ is amino and a formulating agent or a $C_{2-7}$alkanoylating agent is conveniently performed in the absence of a solvent or in a suitable solvent such as a N-methylpyrrolidone or pyridine at ambient or elevated temperature, for example 50°–200° C., preferably 100°–150° C. Examples of formulating agents include formic acid, $C_{1-4}$alkyl formate or $C_{1-4}$alkyl formamide. Examples of $C_{2-7}$alkanoylating agents include acid anhydrides such as acetic, propionic, or n-butyric anhydride or acid halides such as acetyl or propionyl chloride.

The reaction between a compound of the formula (1) wherein $R^2$ is amino and a $C_{1-6}$alkyl isocyanate or the reaction between a compound of formula (4) and ammonia is conveniently performed in an organic solvent such as dioxan, toluene or a halohydrocarbon such as chloroform at ambient or elevated temperature, for example 50°–150° C., preferably at the reflux temperature of the reaction mixture.

A compound of the formula (5) is suitably hydrolysed by reaction with a concentrated acid such as hydrochloric acid in an organic solvent such as a $C_{1-4}$alkanol. Suitably Y is chloro or bromo.

The reaction between a compound of the formula (1) wherein $R^2$ is halo and an amine $HNR^8R^9$ is suitably performed in an organic solvent such as a $C_{1-4}$alkanol at an elevated temperature, for example 50°–120° C., conveniently in a pressure vessel.

A compound of the formula (1) wherein $R^2$ is carboxy is suitably reacted with an excess of $R^5OH$ in the absence of a solvent or in the presence of an inert solvent such as toluene or a halohydrocarbon, at an elevated temperature, for example 40°–120° C., preferably at the reflux temperature of the reaction mixture. A suitable acid catalyst is concentrated sulphuric acid or anhydrous hydrogen chloride.

The reaction of a compound of the formula (1) wherein $R^2$ is $CO_2R^5$ in which $R^5$ is $C_{1-6}$alkyl with $HNR^6R^7$ is suitably performed in water or an organic solvent such as a $C_{1-4}$alkanol or mixtures thereof at ambient or elevated temperature, for example 40°–120° C., conveniently at the reflux temperature of the reaction mixture.

A compound of the formula (1) wherein $R^2$ is —$CONH_2$ is suitably reacted with a dehydrating agent such as phosphorous pentoxide, phosphoryl chloride or thionyl chloride in the absence of a solvent or in an inert organic solvent such as toluene at ambient or elevated temperature, for example 40°–120° C., preferably at the reflux temperature of the reaction mixture. The reaction with phosphoryl chloride may result in the formation of an intermediate chloropyrimidine compound which is suitably hydrolysed to the desired pyrimidone by reaction with glacial acetic acid at elevated temperature, for example 40°–120° C.

The reaction of a compound of the formula (1) wherein $R^2$ is cyano with an azide salt is suitably performed in an organic solvent such as dimethylformamide, dimethylsulfoxide, N-methylpyrrolidine-2-one or tetrahydrofuran at an elevated temperature, for example 40°–200° C., preferably at the reflux temperature of the reaction mixture. Suitable azide salts include ammonium, sodium, potassium or aluminium azide.

A compound of the formula (1) wherein $R^2$ is halo is suitably reacted with a $C_{1-6}$alkoxide salt, such as an alkali metal $C_{1-6}$alkoxide for example sodium ethoxide or sodium methoxide in an organic solvent such as a $C_{1-4}$alkanol at an elevated temperature, for example 50°–140° C., conveniently in a pressure vessel.

A compound of the formula (4) is suitably prepared by reacting a compound of the formula (1) wherein $R^2$ is amino with phosgene or a chemical equivalent thereof. Chemical equivalents of phosgene include trichloromethyl chloroformate or carbonyldiimidazole.

A compound of the formula (5) is conveniently prepared by reaction of a compound of the formula (1) wherein $R^2$ is hydroxy with a halogenating agent such as phosphoryl chloride, thionyl chloride or phosphorous tribromide. Alternatively a compound of the formula (1) wherein $R^2$ is hydroxy is converted to a tosyl derivative which is then reacted in conventional manner with a halide anion, such as fluoride, chloride, bromide or iodide to form a compound of the formula (5).

Compounds of the formula (2) are known or preparable in conventional manner from U.S. Pat. No. 3,819,631.

Pharmaceutically acceptable acid addition salts of the compounds of the formula (1) wherein $R^2$ is —$NR^8R^9$ may be prepared from the corresponding base of the compounds of the formula (1) in conventional manner. For example the base may be reacted with an acid in a $C_{1-4}$alkanol, or an ion-exchange resin may be used. The salts of the compounds of the formula (1) may be interconverted using ion-exchange resins. Non-pharmaceutically acceptable salts are therefore of use as they can be converted to pharmaceutically acceptable salts.

Pharmaceutically acceptable base addition salts of the compounds of the formula (1) may be prepared by standard methods, for example by reacting a solution of the compound of the formula (1) with a solution of the base.

The following biological test methods, data and Examples serve to illustrate this invention.

Bronchodilatation - In vivo

Male guinea-pigs of the Dunkin Hartley strain (500–600g) were anaesthetised with Sagatal (pentobarbital sodium) (60 mg/kg). Airway resistance was measured using a modification of the classical Konzett-Rossler technique (J. pharm. Methods, 13, 309–315, 1985). U46619 (9,11-methanoepoxy-PGH2) was infused i.v. at a rate of 2.5 nmol/min, this produced a steady state of bronchoconstriction (approximately 120% increase from basal airway resistance). The compound under test was administered by i.v. bolus injection, and the subsequent peak inhibition of bronchoconstriction recorded.

The dose of compound required to reduce the U46619-induced bronchoconstriction by 50% is given as the BD50 These results demonstrate in vivo anti-bronchoconstrictor activity.

| COMPOUND | BD$_{50}$ (μmol/kg) |
| --- | --- |
| 5 | 8.34 |
| 16 | 6.03 |
| 18 | 9.70 |

Phosphodiesterase activity

The activity of the compounds of the present invention as inhibitors of a calmodulin insensitive cyclic GMP phosphodiesterase was measured using the procedure described in European Patent Application No. 293063. The compounds of Examples 1 to 24 had IC$_{50}$ values (the concentration of inhibitor required for 50% inhibition of enzyme activity) in the range 0.5 to 88 μM. The compounds of the present invention have the advantage that they are selective in not inhibiting cyclic AMP phosphodiesterase (type III).

Inhibition of spontaneous colonic activity - in vitro

Male albino guinea-pigs (300–400g) were killed by a blow to the back of the head and exsanguinated. A 2cm long segment of the proximal part of the hypogastric loop of the distal colon was rapidly dissected out and placed in oxygenated (95% $O_2$, 5% $CO_2$) modified warm Krebs solution. The tissue was cleaned out with Krebs and the adjoining mesentery discarded. Cotton was then tied to each end and the colon was attached to a tissue holder in an organ bath containing modified oxygenated Krebs solution at 37° C. The other end of the tissue was tied to an isometric transducer and placed under 1 g tension. Force developed by the muscle was detected by the transducer, and recorded on a multi-trace pen recorder. Spontaneous colonic activity, as assessed by the contraction distance over a five minute period, was subjected to computer analysis.

The tissues were allowed to settle at a resting tension of 1 g for 1 hour, during which time they were washed at 15 minute intervals. Three samples of pre-dose activity were taken and averaged. The tissues were then dosed and two samples of post-dose activity were taken. The lowest value was used to calculate the percentage relaxation, and log dose response curves were constructed. The tissues were washed 10 minutes after dosing and left for 15 minutes to settle prior to the next control period.

The concentration of compound required to reduce spontaneous colonic activity by 50% is given as the IC$_{50}$.

| COMPOUND | IC$_{50}$ (μM) |
| --- | --- |
| 5 | 2.4 |
| 15 | 0.75 |
| 18 | 3.3 |
| 21 | 3.7 |

EXAMPLE 1

6-Amino-2-(2-propoxyphenyl)pyrimidin-4[3H]-one

Ethyl cyanoacetate (4.52 g) was added to a stirred solution of 2-propoxybenzamidine in ethanol (prepared from sodium, 1.84 g., in ethanol, 100 ml. and 2-propoxybenzamidine methanesulphonate, 11.61 g). The reaction mixture was stirred at ambient temperature for 18 hours and then evaporated under reduced pressure to leave a residue which was dissolved in water. The aqueous solution was extracted with diethyl ether (2×25 ml) and the combined ether extracts were washed with water. The combined aqueous phase was treated with glacial acetic acid to pH 5 to precipitate a crude product. Further crude product was obtained by extracting the ether extracts with 1 normal sodium hydroxide (2×30 ml) and acidifying the combined alkaline extracts with glacial acetic acid to pH 5. The combined crude product was recrystallised from isopropanol to yield the title compound, 2.34 g, m.p. 183.5°–184.5° C.

EXAMPLE 2

6-Acetamido-2-(2-propoxyphenyl)pyrimidin-4[3H]-one

A stirred solution of 6-amino-2-(2-propoxyphenyl)-pyrimidin-4[3H]-one (0.5 g) and acetic anhydride was heated under reflux for 2.5 hours. The cooled reaction mixture was evaporated under reduced pressure to yield a residue which was washed with water and recrystallised twice from methanol to yield the title compound, 0.29 g, m.p. 230°–1° C.

EXAMPLE 3

6-Propionamido-2-(2-propoxphenyl)pyrimidin-4[3H1 one

A stirred solution of 6-amino-2-(2-propoxyphenyl)-pyrimidin-4[3H]-one (0.50 g) and propionic anhydri was heated at 140° C. for 2.5 hours. Water and ethanol was added to the cooled reaction mixture which was then evaporated under reduced pressure to half volume. A precipitate was collected, washed with water and recrystallised from ethanol to yield the title compound, 0.41 g, m.p. 228°–9° C.

EXAMPLE 4

6-Butyramido-2-(2-propoxyphenyl)pyrimidin-4[3H1 one

A stirred solution of 6-amino-2-(2-propoxyphenyl)-pyrimidin-4[3H]-one (0.68 g) and n-butyric anhydri was heated at 140° C. for 5 hours. Ethanol was added to the cooled reaction mixture which was then evaporated under reduced pressure to yield a residue which was azeotroped and washed with water. The residue was eluted from silica with chloroform and the combined fractions containing product were evaporated under reduced pressure to yield a crude product which was recrystallised from isopropanol: diethyl ether to yield the title compound, 0.21 g, m.p. 177°–8° C.

EXAMPLE 5

6-N'-Methylureido-2-(2-propoxyphenyl)pyrimidin-4[3H}-one

A stirred solution of 6-amino-2-(2-propoxyphenyl)-pyrimidin-4[3H]-one (0.61 g) and methyl isocyanate in dioxan was heated under reflux for 3 hours. A second quantity of methyl isocyanate (0.114 g) was added and the reaction mixture was heated under reflux for a further 2 hours. A third quantity of methyl isocyanate (0.28 g) was added and the reaction mixture was heated under reflux for 16 hours. A final quantity of methyl isocyanate (0.28 g) was added and stirring under reflux continued for 7 more hours. The cooled reaction mixture was evaporated under reduced pressure to yield a crude product which was purified by using column chromatography and by recrystallisation from methanol to yield the title compound, 0.18 g, m.p. 234°-5° C.

EXAMPLE 6

4,6-Dihydroxy-2-(2-propoxyphenyl)pyrimidine

A stirred mixture of diethyl malonate (17.62 g), 2-propoxybenzamidine methanesulphonate (29.03 g) and sodium ethoxide in ethanol (from sodium, 6.9 g, and ethanol, 150 ml) was heated under reflux for 6 hours. The cooled reaction mixture was evaporated under reduced pressure to yield a residue which was dissolved in water. Concentrated hydrochloric acid was added to the aqueous solution to yield the title compound, 21.56 g. A sample (0.5 g) of this material was recrystallised twice from methanol to yield the pure title compound, 0.119 g, m.p. 224°-5° C.

EXAMPLE 7

4-Chloro-6-hydroxy-2-(2-propoxyphenyl)pyrimidine a) A stirred solution of 4,6-dihydroxy-2-(2-propoxyphenyl)pyrimidine (21.05 g) and phosphoryl chloride (65.8 g) was heated under reflux for 1.5 hours. Excess phosphoryl chloride was removed under reduced pressure and the residue was added to ice. The resultant mixture was extracted with chloroform (200 ml and 2×100 ml) and the combined chloroform extracts were washed with water, dried (magnesium sulphate) and evaporated under reduced pressure. The residue was eluted from silica with ether to yield 4,6-dichloro-2-(2-propoxyphenyl)pyrimidine, 20.69 g.

b) A stirred solution of 4,6-dichloro-2-(2-propoxyphenyl)pyrimidine (16.68 g) in concentrated hydrochloric acid (40 ml), n-butanol (80 ml) and water (40 ml) was heated under reflux for 3 hours. The cooled reaction mixture was evaporated under reduced pressure to yield a residue which was washed with water and diethyl ether and recrystallised from isopropanol to yield the title compound, 8.46 g, m.p. 115.5°-11 6.5° C. A sample (1 g) of this material was recrystallised twice from isopropanol to yield the pure title compound, 0.42 g, m.p. 118°-118.5° C.

EXAMPLE 8

6-Ethylamino-2-(2-propoxyphenyl)pyrimidin 4[3H1-one

4-Chloro-6-hydroxy-2-(2-propoxyphenyl)pyrimidine (0.66 g) and ethylamine in ethanol (33%, 20 ml) was heated at 90° C. in a pressure vessel for 16 hours. The cooled reaction mixture was evaporated under reduced pressure to yield an oil which solidified on trituration with diethyl ether. The residue was recrystallised from isopropanol: diethyl ether, washed with water and recrystallised from isopropanol:water to yield the title compound, 0.47 g, m.p. 187°-8° C.

EXAMPLE 9

6-Propylamino-2-(2-propoxyphenyl]pyrimidin-4[3H1-one

4-Chloro-6-hydroxy-2-(2-propoxyphenyl)pyrimidine (0.66 g), n-propylamine (1.8 g) and ethanol (20 ml) was heated at 90° C. in a pressure vessel for 16 hours. The cooled reaction mixture was evaporated under reduced pressure to lo yield an oil which solidified on washing with water. The residue was recrystallised from isopropanol: water to yield the title compound, 0.56 g. m.p. 172°-3° C.

EXAMPLE 10

6-(2-Hydroxyethylamino)-2-(2-propoxyphenyl)pyrimidin-4[3H1-one

A stirred solution of 4-chloro-6-hydroxy-2-(2-propoxyphenyl)pyrimidine (0.43 g) and ethanolamine (0.3 g) in n-butanol (8 ml) was heated under reflux for 4 hours. The cooled reaction mixture was evaporated under reduced pressure to yield a residue which was washed with diethyl ether and then eluted from silica with chloroform: methanol (gradient elution). The combined fractions containing product were evaporated under reduced pressure to yield a crude product which was recrystallised from isopropanol:diethyl ether to yield the title compound, 0.28 g, m.p. 164.5°-65.5° C.

EXAMPLE 11

6(3-Hydroxypropylamino)-2-(2-propoxyphenyl)-primidin-4[3H-one

A stirred solution of 4-chloro-6-hydroxy-2-(2-propoxyphenyl)pyrimidine (0.66 g) and 3-amino-1-propanol (0.56 g) in n-propanol was heated under reflux for 16 hours. The cooled reaction mixture was evaporated under reduced pressure to yield an oil which was partitioned between chloroform (20 ml) and water (20 ml). The chloroform layer was separated from the aqueous layer which was extracted with chloroform (2×10 ml) and the combined chloroform layers were washed with water, dried (magnesium sulphate) and evaporated under reduced pressure. The residue was recrystallised from isopropanol:diethyl ether to yield the title compound, 0.54 g, m.p. 147.5°-148.5° C.

EXAMPLE 12

4-Hydroxy-6-methyl-2 (2-propoxyphenyl)pyrimidine

A stirred mixture of ethyl acetoacetate (0.72 g) 2-propoxybenzamidine methanesulphonate (1.45 g) and sodium ethoxide in ethanol (from sodium, 0.34 g, and ethanol, 10 ml) was heated under reflux for 22 hours. The cooled reaction mixture was evaporated under reduced pressure and the residue was dissolved in water. The aqueous solution was acidified with concentrated hydrochloric acid and extracted with chloroform (3×15 ml). The combined chloroform extracts were dried (magnesium sulphate) and evaporated under reduced pressure to yield a residue which was recrystallised from isopropanol:diethyl ether to yield the title compound, 0.65 g, m.p. 109°-110.5° C.

EXAMPLE 13

6-Hydroxy-2-(2-propoxyphenyl)pyrimidine-4-carboxylic acid

A solution of 2-propoxybenzamidine methanesulphonate (2.9g), 10% sodium hydroxide (4 ml) and ethyl 4-oxalacetate (1.6g) in water (8 ml) was stirred at ambient temperature for 42 hours. The reaction mixture was evaporated to dryness to yield a crude product which was washed with dilute hydrochloric acid and water to 5 yield the title compound, 0.82g, m.p. 179.5°-181.5° C. A sample (0.4g) was recrystallised from ethanol to yield the pure title compound, 0.24 g, m.p. 184°-5° C.

EXAMPLE 14

Ethyl 6-hydroxy-2-(2-propoxyphenyl)pyrimidine-4-carboxylate

A stirred solution of 6-hydroxy-2-(2-propoxyphenyl) pyrimidine-4-carboxylic acid (1.06g) in ethanol and concentrated sulphuric acid (0.5 ml) was heated under reflux for 3 hours. Most of the ethanol was removed under reduced pressure, then ice-water was added to the residue. The mixture was made alkaline (pH 10-11) with sodium carbonate solution and then extracted with chloroform (3×25 ml). The combined chloroform extracts were washed with water, dried (magnesium sulphate) and evaporated under reduced pressure to yield after washing with petroleum ether (b.p. 40°–60°) the title compound, 0.85g, m.p. 135.5°–137° C. A sample (0.4g) was recrystallised from ethanol to yield the pure title compound, 0.22g, m.p. 137°–8° C.

EXAMPLE 15

6-Hydroxy-2-(2-propoxyphenyl)pyrimidine-4-carboxamide

A solution of ethyl 6-hydroxy-2-(2-propoxyphenyl) pyrimidine-4-carboxylate (0.44g) in aqueous ammonia solution (20 ml) was stirred in a stoppered flask at ambient temperature for 4 hours and then allowed to stand for 3 days. The reaction mixture was acidified with concentrated hydrochloric acid to precipitate the title compound, 0.46 g, m.p. 232°–4° C. This was recrystallized from ethanol:methanol to yield the pure title compound, 0.32g, m.p. 233.5°–234°–5° C.

EXAMPLE 16

4-cyano-6-hydroxy-2-(2-propoxyphenyl)pyrimidine

A stirred solution of 6-hydroxy-2-(2-propoxyphenyl)-pyrimidine-4-carboxamide (0.50 g) in phosphoryl chloride (16 ml) was heated under reflux for 4 hours and then the reaction mixture was evaporated under reduced pressure to remove excess phosphoryl chloride. Water was added to the residue, which was extracted with chloroform (3×20 ml). The combined extracts were washed with water, dried (magnesium sulphate) and evaporated under reduced pressure to yield an oil which was heated on a steam bath with glacial acetic acid (15 ml) for 4 hours. The cooled reaction mixture was evaporated under reduced pressure to yield a crude product which was combined with further product similarly prepared from 6-hydroxy-2-(2-propoxyphenyl)pyrimidine-4-carboxamide (0.82 g) and phosphoryl chloride (25 ml). The combined products were eluted from silica with ether:chloroform (9:1) and fractions containing product were combined and evaporated under reduced pressure to yield the title compound, 0.31 g, m.p. 135°–6° C., (from isopropanol/ether).

EXAMPLE 17

2-(2-Propoxyphenyl)-6-(1H-tetrazol-5-yl)pyrimid-4-(3H)-one

A stirred solution of 4-cyano-6-hydroxy-2-(2-propoxyphenyl)pyrimidine (325 mg), sodium azide (91 mg) and ammonium chloride (75 mg) in dimethylformamide (15 ml) was heated at 125° C. for 5 hours. Most of the dimethylformamide was removed under reduced pressure and water added to the oily residue which solidified. The mixture was cooled and the solid was collected, washed with water and recrystallised from glacial acetic acid to yield the title compound, 174 mg, m.p. 219°–221° C.

EXAMPLE 18

4-Ethyl-6-hydroxy-2-(2-propoxyphenyl)pyrimidine

A solution of ethyl propionylacetate (0.79 g), 2-propoxybenzamidine methanesulphonate (1.45 g) and sodium hydroxide (0.60 g) in water (5 ml) and ethanol (5 ml) was stirred at ambient temperature for 22 hours. Most of the solvent was removed under reduced pressure and water (20 ml) was added. The mixture was acidified to pH 2 with concentrated hydrochloric acid and then extracted with chloroform (3×30 ml). the combined extracts were washed with dilute acetic acid, dried (magnesium sulphate) and evaporated under reduced pressure to yield a residue which was recrystallised twice from ether to yield the title compound, 373 mg, m.p. 97°–98.5° C.

EXAMPLE 19

4-Hydroxy-6-phenyl-2-(2-propoxyphenyl)pyrimidine

In a manner similar to that of Example 18, 2-propoxybenzamidine methanesulphonate (1.45 g) and ethyl benzoylacetate (1.19 g) yielded the title compound, 0.49 g, m.p. 163°–164.5° C. (from isopropanol).

EXAMPLE 20

N-Methyl 6-hydroxy-2-(2-propoxyphenyl)pyrimidine-4-carboxamide

A solution of ethyl 6-hydroxy-2-(2-propoxyphenyl)-pyrimidine-4-carboxylate (0.40 g) and methylamine in industrial methylated spirit (33%, 15 ml) in ethanol (15 ml) was stirred at ambient temperature for 6 hours and then allowed to stand for 3 days. The reaction mixture was evaporated under reduced pressure to yield a crude product which was recrystallised from ethanol to yield the title compound, 0.26 g, m.p. 165°–6° C.

EXAMPLE 21

N-Ethyl 6-hydroxy-2-(2-propoxyphenyl)pyrimidine-4-carboxamide

In a manner similar to that of Example 20, ethyl 6-hydroxy-2-(2-propoxyphenyl)pyrimidine-4-carboxylate (0.4 g) and ethylamine in ethanol (33%, 15 ml) yielded the title compound, 0.31 g, m.p. 182.5°–183.5° C. (from ethanol).

EXAMPLE 22

N-Propyl 6-hydroxy-2-(2-propoxyphenyl)pyrimidine-4-carboxamide

In a manner similar to that of Example 20, ethyl 6-hydroxy-2-(2-propoxyphenyl)pyrimidine-4-carboxylate (0.40 g), propylamine (5 ml) and ethanol (10 ml) yielded the title compound, 0.35 g, m.p. 194.5° C. (from isopropanol).

EXAMPLE 23

6-Ethoxy-2-(2-propoxyphenyl)pyrimidin-4(3H)-one

A stirred solution of 4-chloro-6-hydroxy-2-(2-propoxyphenyl)pyrimidone (0.5 g) and sodium ethoxide (from 0.18 g sodium) in ethanol (25 ml) was heated in a pressure vessel at 125° C. for 24 hours. The residue left after evaporation was dissolved in water (20 ml), acetic acid was added to precipitate a gum, and the mixture was extracted with chloroform. Evaporation of the extract gave a solid which was recrystallised from ether to yield the title compound, 0.07 g, m.p. 95.5°–97° C.

EXAMPLE 24

6-N,N-Bis-(2-hydroxyethyl)amino-2-(2-propoxyphenyl)pyrimid-in-4-(3H)-one

A stirred solution of 4-chloro-6-hydroxy-2(2-propoxyphenyl)pyrimidine (0.32 g) and diethanolamine (0.4 g) in 1-propanol (8 ml) was heated under reflux for 17 hours. The residue left after evaporation was purified by flash chromatography (silica, 5% methanol in chloroform) and the major product was recrystallised from 2-propanol to yield the title compound, 0.16 g, m.p. 111°–112° C.

EXAMPLE 25

Pharmaceutical compositions for oral administration are prepared by combining the following :

|  | % w/w |  |  |
| --- | --- | --- | --- |
| 6-N'-methylureido-2-(2-propoxyphenyl)pyrimidin-4[3H]-one | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

EXAMPLE 26

A pharmaceutical composition for parenteral administration is prepared by dissolving the title compound of Example 15 (0.02 g) in polyethylene glycol 300 (25 ml) with heating. This solution is then diluted with water for injections Ph. Eur. (to 100 ml). The solution is then sterilized by filtration through a 0.22 micron membrane filter and sealed in sterile containers.

What is claimed is:

1. A compound of the formula (1):

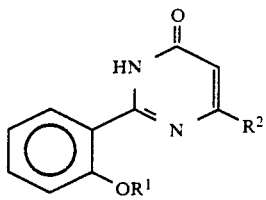

or a pharmaceutically acceptable salt thereof, wherein
R$^1$ is C$_{1-6}$alkyl, C$_{2-6}$alkenyl, C$_{3-5}$cycloalkylC$_{1-6}$alkyl, phenylC$_{1-6}$alkyl or C$_{1-6}$alkyl substituted by 1 to 6 fluoro groups; and
R$^2$ is phenyl, C$_{1-6}$alkoxy, halo —NHCOR$^3$, —NHCONHR$^4$, cyano, —CONR$^6$R$^7$, or NR$^8$R$^9$ wherein R$^3$ to R$^7$ are independently hydrogen or C$_{1-6}$alkyl and R$^8$ and R$^9$ are independently hydrogen or C$_{1-6}$alkyl optionally substituted by hydroxy provided that the carbon atom adjacent to the nitrogen atom is not substituted by hydroxy and further provided that R$^8$ and R$^9$ are not both hydrogen.

2. A compound according to claim 1 wherein R$^1$ is C$_{2-5}$alkyl.

3. A compound according to claim 1 wherein R$^1$ is C$_{3-5}$alkenyl.

4. A compound according to claim 1 wherein R$^1$ is n-propyl.

5. A compound according to claim 1 wherein R$^2$ is phenyl.

6. A compound according to claim 1 wherein R$^2$ is C$_{1-6}$alkoxy or halo.

7. A compound according to claim 1 wherein R$^2$ is —NHCOR$^3$ or —NHCONHR$^4$.

8. A compound according to claim 1 wherein R$^2$ is cyano or —CONR$^6$R$^7$.

9. A compound according to claim 1 wherein R$^2$ is —NR$^8$R$^9$.

10. A compound according to claim 1 which is selected from the group consisting of:
6-acetamido-2-(2-propoxyphenyl)pyrimidin-4[3H]-one,
6-propionamido-2-(2-propoxyphenyl)pyrimidin-4[3H]-one,
6-butyramido-2-(2-propoxyphenyl)pyrimidin-4[3H]-one,
6-N'-methylureido-2-(2-propoxyphenyl)pyrimidin-4[3H]-one,
4-chloro-6-hydroxy-2-(2-propoxyphenyl)pyrimidine,
6-ethylamino-2-(2-propoxyphenyl)pyrimidin-4[3H]-one,
6-propylamino-2-(2-propoxyphenyl)pyrimidin-4[3H]-one,
6-(2-hydroxyethylamino)-2-(2-propoxyphenyl)-pyrimidin-4[3H]-one,
6-(3-hydroxypropylamino)-2-(2-propoxyphenyl)-pyrimidin-4[3H]-one,
6-hydroxy-2-(2-propoxyphenyl)pyrimidine-4-carboxamide,
4-cyano-6-hydroxy-2-(2-propoxyphenyl)pyrimidine,
4-hydroxy-6-phenyl-2-(2-propoxyphenyl)pyrimidine,
N-methyl 6-hydroxy-2-(2-propoxyphenyl)pyrimidine-4-carboxamide,
N-ethyl 6-hydroxy-2-(2-propoxyphenyl)pyrimidine-4-carboxamide,
N-propyl 6-hydroxy-2-(2-propoxyphenyl)pyrimidine-4-carboxamide,
6-ethoxy-2-(2-propoxyphenyl)pyrimidin-4(3H)-one, or
6-N,N-bis-(2-hydroxyethyl)amino-2-(2-propoxyphenyl)pyrimidin-4(3H)-one,
or a pharmaceutically acceptable salt thereof.

11. A pharmaceutical composition which comprises an effective amount of a compound of the formula is:

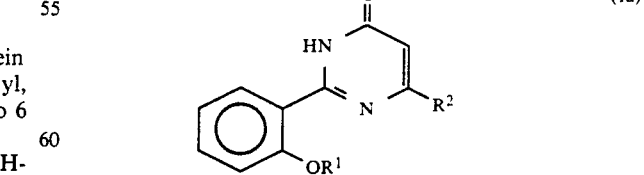

wherein
R$^1$ is C$_{1-6}$alkyl, C$_{2-6}$alkenyl, C$_{3-5}$cycloalkylC$_{1-6}$alkyl, phenylC$_{1-6}$alkyl or C$_{1-6}$alkyl substituted by 1 to 6 fluoro groups; and
is C$_{1-6}$alkyl, phenyl, hydroxy, C$_{1-6}$alkoxy, halo —NHCOR$^3$, —NHCONHR$^4$, cyano, —CONR⁶R⁷, or NR⁸R⁹ wherein $R^3$ to $R^7$ are independently hydrogen or $C_{1-6}$alkyl and $R^8$ and $R^9$ are independently hydrogen or $C_{1-6}$alkyl optionally substituted by hydroxy provided that the carbon atom adjacent to the nitrogen atom is not substituted by hydroxy and further provided that $R^2$ is not $C_{1-6}$alkyl or hydroxy when $R^1$ is methyl, or a pharmaceutically acceptable salt thereof and a pharmaceutically acceptable carrier.

12. A method of effecting bronchodilation in a host in need thereof by administration of a non-toxic but effective amount of a composition as defined in claim 11.

* * * * *